(12) United States Patent
Tanaka et al.

(10) Patent No.: US 10,258,990 B2
(45) Date of Patent: Apr. 16, 2019

(54) IMAGING LITTLE FISH MANAGEMENT DEVICE AND LITTLE FISH IMAGING PLATE USED IN THE SAME

(71) Applicants: NATIONAL UNIVERSITY CORPORATION MIE UNIVERSITY, Mie (JP); HASHIMOTO ELECTRONIC INDUSTRY CO., LTD., Mie (JP)

(72) Inventors: Toshio Tanaka, Tsu (JP); Yasuhito Shimada, Tsu (JP); Noriko Umemoto, Tsu (JP); Masaru Obata, Matsusaka (JP); Masatoshi Hashimoto, Matsusaka (JP)

(73) Assignee: NATIONAL UNIVERSITY CORPORATION MIE UNIVERSITY, Mie (JP)

( * ) Notice: Subject to any disclaimer, the term of this patent is extended or adjusted under 35 U.S.C. 154(b) by 867 days.

(21) Appl. No.: 14/674,486

(22) Filed: Mar. 31, 2015

(65) Prior Publication Data

US 2016/0023207 A1    Jan. 28, 2016

(30) Foreign Application Priority Data

Jul. 24, 2014 (JP) .................. 2014-150299

(51) Int. Cl.
*B01L 3/00* (2006.01)
*A61D 7/00* (2006.01)
(Continued)

(52) U.S. Cl.
CPC ............ *B01L 3/5085* (2013.01); *A01K 61/90* (2017.01); *A61B 5/0059* (2013.01); *A61D 3/00* (2013.01);
(Continued)

(58) Field of Classification Search
CPC .......... B01L 3/5085; B01L 2300/0618; B01L 2300/0654; B01L 2300/0829;
(Continued)

(56) References Cited

U.S. PATENT DOCUMENTS 6,913,732 B2 * 7/2005 Sha ........................ B01L 3/5025
117/206
7,501,279 B2 * 3/2009 Folch .................. B01L 3/50255
435/297.5
(Continued)

FOREIGN PATENT DOCUMENTS

JP        2014169951 A        9/2014

*Primary Examiner* — Benjamin R Whatley
(74) *Attorney, Agent, or Firm* — Duane Morris LLP

(57) ABSTRACT

An imaging plate includes a plurality of wells individually accommodating little fishes, and the little fishes inside the wells are imaged from bottom portions of the wells. In order to adjust imaging posture or imaging positions of the little fishes inside the wells, an imaging little fish management device includes a water unit which supplies and discharges water into and from each well of the imaging plate. The water inside each well flows through a discharge hole provided laterally at a lowermost portion of each well. The water unit is also used to breed the little fishes of the wells of the imaging plate.

11 Claims, 10 Drawing Sheets

(51) Int. Cl.
*A61B 5/00* (2006.01)
*A61D 3/00* (2006.01)
*A01K 61/90* (2017.01)

(52) U.S. Cl.
CPC ............ *A61D 7/00* (2013.01); *A61B 2503/40* (2013.01); *B01L 2300/0618* (2013.01); *B01L 2300/0654* (2013.01); *B01L 2300/0829* (2013.01); *B01L 2300/0854* (2013.01)

(58) Field of Classification Search
CPC ... B01L 2300/0854; A01K 61/90; A61D 3/00; A61D 7/00; A61B 5/0059; A61B 2503/40
USPC ...................................................... 422/82.05
See application file for complete search history.

(56) References Cited

U.S. PATENT DOCUMENTS

| 2006/0018833 | A1* | 1/2006 | Murphy | ............. | A61K 49/0008 |
| | | | | | 424/9.2 |
| 2007/0178012 | A1* | 8/2007 | Ferrante | ................ | B01L 3/5085 |
| | | | | | 422/82.05 |
| 2011/0294215 | A1* | 12/2011 | Applegate | .............. | C12M 23/30 |
| | | | | | 435/401 |

* cited by examiner

IMAGING LITTLE FISH MANAGEMENT DEVICE AND LITTLE FISH IMAGING PLATE USED IN THE SAME

CROSS-REFERENCE TO RELATED APPLICATION

This application claims benefit under 35 U.S.C. 119 of JP2014-150299 filed on Jul. 24, 2014, the title of IMAGING LITTLE FISH MANAGEMENT DEVICE AND LITTLE FISH IMAGING PLATE USED IN THE SAME the entire content of which is incorporated herein reference.

BACKGROUND

1. Technical Field

The present invention relates to an imaging little fish management device capable of individually observing or imaging a plurality of little fishes and a little fish imaging plate used in the same.

2. Related Art

The use of zebrafishes has gained attention in a medical field and a pharmacy field. As an example, after eggs of gene-injected zebrafishes are hatched and bred, the shapes and the like of the adult fishes are visually checked or imaged. As another example, after immature zebrafishes are bred while a specific medical agent is introduced into their living water system, a fish shape or a partial tissue shape is visually checked or imaged. Since the zebrafishes are small and grow fast, the zebrafishes can be highly efficiently used as a plurality of kinds of subjects. Further, an ethical issue on animals is also relieved.

In order to observe or image the zebrafishes, an imaging device such as a microscope or an electronic imaging device is used. However, since the zebrafishes are very small, there has been a problem in sequential observation or imaging of the plurality of zebrafishes, which burdens a skilled worker with a heavy workload.

In order to highly efficiently image specific regions of the plurality of zebrafishes, an imaging plate which includes a well array having wells formed in a matrix shape and depressed is used. The zebrafishes are separately disposed in the plurality of wells by using a tool such as a pipette or a pincette. In order to suppress the deterioration of zebrafish living conditions, it is favorable that some water be held in each well.

In imaging work including observation or imaging, it is preferable that illumination light irradiation be performed from the bottom surface side of the imaging plate and reflected light or fluorescence from the zebrafishes is sent from the bottom surface side of the imaging plate to an imaging system. The imaging plate is shifted by the pitch of one well in a direction perpendicular to an optical axis of the imaging system. Accordingly, the zebrafish inside each well is highly efficiently observed or imaged.

In order to satisfactorily image a specific region of each zebrafish, it is preferable to lay the zebrafish on a center portion of a bottom surface of each well. Further, in order to simplify image processing, it is preferable to arrange the zebrafishes such that the longitudinal direction from the head to the tail of each zebrafish (hereinafter, referred to as a head-to-tail direction) becomes the same direction. However, there has been a problem in work of correcting a position and posture to lay each zebrafish on the center portion of the bottom surface of the well while each zebrafish is arranged in the same direction, which is very troublesome and easily damages the zebrafishes.

In order to solve this problem, US 2007/0178012 and JP 2014-169951 A (published on Sep. 8, 2014 by HASHIMOTO ELECTRONIC INDUSTRY CO., LTD and the like) adopt a side viewing optical system capable of imaging zebrafishes from the lateral directions of wells. According to the side viewing optical system, the zebrafishes which are not lying can be satisfactorily viewed from the sides thereof. However, since the side viewing optical system needs a reflection surface for deflecting an optical axis, a structure of an imaging plate becomes complex. Further, it has been found that there is a problem of a degraded image due to dirt or the like on the reflection surface.

Further, when the zebrafishes as subjects are sequentially put into the wells of the imaging plate by using a manipulation tool such as a pipette or a pincette, there has been a case where the zebrafishes are damaged. Moreover, there has been a case where contamination unfavorable for the zebrafishes happens through the manipulation tool.

In order to solve this problem, it is desirable to grow the zebrafishes while separately putting the zebrafishes into the wells at the immature stage and thereafter giving a medical agent and the like necessary for each immature fish. However, management of water including treatment of feces becomes essential for breeding of the zebrafishes. Further, it becomes essential to put an anesthetic solution during imaging and to replace breeding water after the imaging. In the related art, an imaging plate capable of managing water in this way is not known.

SUMMARY

An object of the present invention is to provide an imaging little fish management device capable of efficiently performing little fish imaging work of sequentially imaging optical examination little fishes separately accommodated in a plurality of wells of an imaging plate. Another object of the present invention is to provide a little fish imaging plate used in the imaging little fish management device and capable of efficiently performing the little fish imaging work.

Hereinafter, an example will be described in which zebrafishes are used as optical examination little fishes. The imaging little fish management device of the present invention uses an imaging plate in which a plurality of wells individually accommodating the zebrafishes is arranged in a matrix shape, as in the related art. The imaging plate includes a transparent bottom portion which faces each well and a partition wall portion which defines each well, and an upper end of each well is opened.

A scanning unit sequentially moves the imaging plate, preferably in the horizontal direction, that is, the direction perpendicular to the thickness direction of the imaging plate, and an imaging unit sequentially images each zebrafish, preferably, lying on the bottom portion.

Particularly, the imaging little fish management device of the present invention performs a preliminary water discharge operation for, before an imaging operation, discharging water inside each of the wells through a discharge hole which is located in the vicinity of a boundary portion between the partition wall portion and the bottom portion and which does not enable each of the little fishes to pass therethrough. Due to a downward water stream or a decreased water level formed by the preliminary water discharge operation, each zebrafish inside each well is easily guided and settled onto the bottom portion. Therefore, a target region of each zebrafish can be clearly imaged without adjusting a focus of the imaging unit.

Further, since a position or posture of each zebrafish can be adjusted by the water stream formed by the preliminary water discharge operation, it becomes easy to observe or image the zebrafishes. Since the discharge hole is not formed in the transparent bottom portion, the discharge hole does not become an obstacle to the imaging. Moreover, no zebrafish escapes to the outside from the discharge hole.

Further, since water can be supplied to the wells by preliminarily discharging the water of the wells, the water of the wells can consequently be replaced. As a result, the little fishes inside the wells can be bred for a long period of time. This means that the little fishes can be imaged in time series for a long period of time.

In a preferred aspect, an anesthesia operation for adding an anesthetic solution to the water inside the wells is performed before the preliminary discharge operation, and an awakening operation for supplying fresh water to the wells is performed after the imaging operation. Accordingly, the anesthesia operation for improving the imaging resolution can be simply performed.

In a preferred aspect, after the preliminary water discharge operation, a water supply operation for causing water to reversely flow into the wells through the discharge holes, and thereafter a secondary water discharge operation for discharging the water inside the wells through the discharge holes is performed. Accordingly, the zebrafishes stuck to the partition wall portions of the wells by the preliminary water discharge operation can be settled onto the bottom portions again. Further, since the water is discharged and supplied from the boundary portion between the partition wall portion and the bottom portion through the common discharge hole, there is no need to provide an independent water supply hole, and a structure of the imaging plate can be simplified and downsized.

In a preferred aspect, a little fish arrangement operation for sequentially executing the preliminary water discharge operation, the water supply operation, and the secondary water discharge operation is performed, and thereafter the little fishes of the wells are imaged. Next, the obtained images are processed and it is determined whether a little fish arrangement state is good or not. Next, the little fish arrangement operation is performed again on at least the little fishes being in a poor arrangement state. Accordingly, the arrangement state of each little fish can be largely improved.

In a preferred aspect, the partition wall portion includes an inclined surface portion which is inclined in a tapered shape toward the bottom portion. Preferably, the inclined surface portion is provided in a lower portion of each well. Accordingly, the zebrafishes become easily settled onto the bottom portion.

In a preferred aspect, a long side edge of the substantially rectangular bottom portion is formed so as to be longer than an estimated maximum length of the zebrafish. Further, a short side edge of the bottom portion is formed so as to be shorter than the estimated maximum length of the zebrafish. Further, the bottom portions are arranged in a matrix shape in a direction where the longitudinal directions thereof match one another. Accordingly, the zebrafishes inside the wells become easily settled in the substantially parallel direction to one another.

In a preferred aspect, the water discharge hole is formed adjacent to the long side edge of the bottom portion. Accordingly, the zebrafishes become easily laid on the bottom portion by the water stream caused by the water discharged or supplied through the discharge hole. Although it is preferable that the discharge hole be provided only along one of the pair of long side edges of the bottom portion, the discharge hole can also be provided along both the pair of long side edges of the bottom portion. Further, an upper surface of the bottom portion being in contact with each well can also be provided in a concave lens shape. Accordingly, the zebrafishes become easily guided to a center portion of the bottom portion.

In a preferred aspect, a water storage sub-well is provided adjacent to the side of each well, and the sub-well and the well in a pair communicate with each other by the discharge hole. Accordingly, the water can be easily supplied to and discharged from each well while the water in each well is independently maintained. Further, it becomes easy to anesthetize the zebrafishes inside the wells.

In a preferred aspect, an overflow bottom wall portion is provided between the well and the sub-well which are adjacent to each other. The overflow bottom wall portion is formed so as to be lower than the partition wall portion provided between the wells. Accordingly, it is possible to prevent the water inside the sub-well from overflowing into the adjacent well through the partition wall portion when the water is supplied (caused to reversely flow) from the sub-well to the well through the discharge hole.

In a preferred aspect, the imaging plate includes a concave portion which is defined by the partition wall portion. Further, a cylindrical auxiliary tube member including the well is inserted into the concave portion. Accordingly, the sub-well is automatically formed between the partition wall portion and a peripheral wall portion of the auxiliary tube member. Preferably, the peripheral wall portion of the auxiliary tube member includes the overflow bottom wall portion. In addition, the well and the sub-well can also be integrally formed with each other.

In a preferred aspect, the water is supplied to the sub-well and is discharged from the sub-well by a plurality of nozzles individually drooped to the plurality of adjacent sub-wells. Accordingly, the water can be easily supplied to and discharged from each sub-well in an independent manner. Note that, preferably, the plurality of nozzles can be arranged in series in one direction among two directions of a direction parallel to an upper surface of the imaging plate and a direction perpendicular to the upper surface thereof. As a result, the imaging plate is shifted by the pitch of one well in the other direction perpendicular to the one direction, whereby the water can be supplied to and discharged from each well by a simple structure. The water supply nozzle and the water discharge nozzle can be separately configured, and a nozzle for both water suction and discharge can also be adopted.

In a preferred aspect, the discharge hole has a cross-sectional shape that enables prey for each little fish and feces of each little fish to pass therethrough, and the water inside the wells is periodically replaced or circulated. Accordingly, since the water inside each well can be kept clean, and hence each zebrafish to be imaged can be grown inside each well. The water which is discharged from the wells can be cleaned, for example, by filtration using a filter. As a result, the zebrafishes at respective growth stages can be easily imaged.

The little fish imaging plate can be preferably used in the imaging little fish management device, but can also be used for other application.

DESCRIPTION OF EMBODIMENTS

Figure 1:
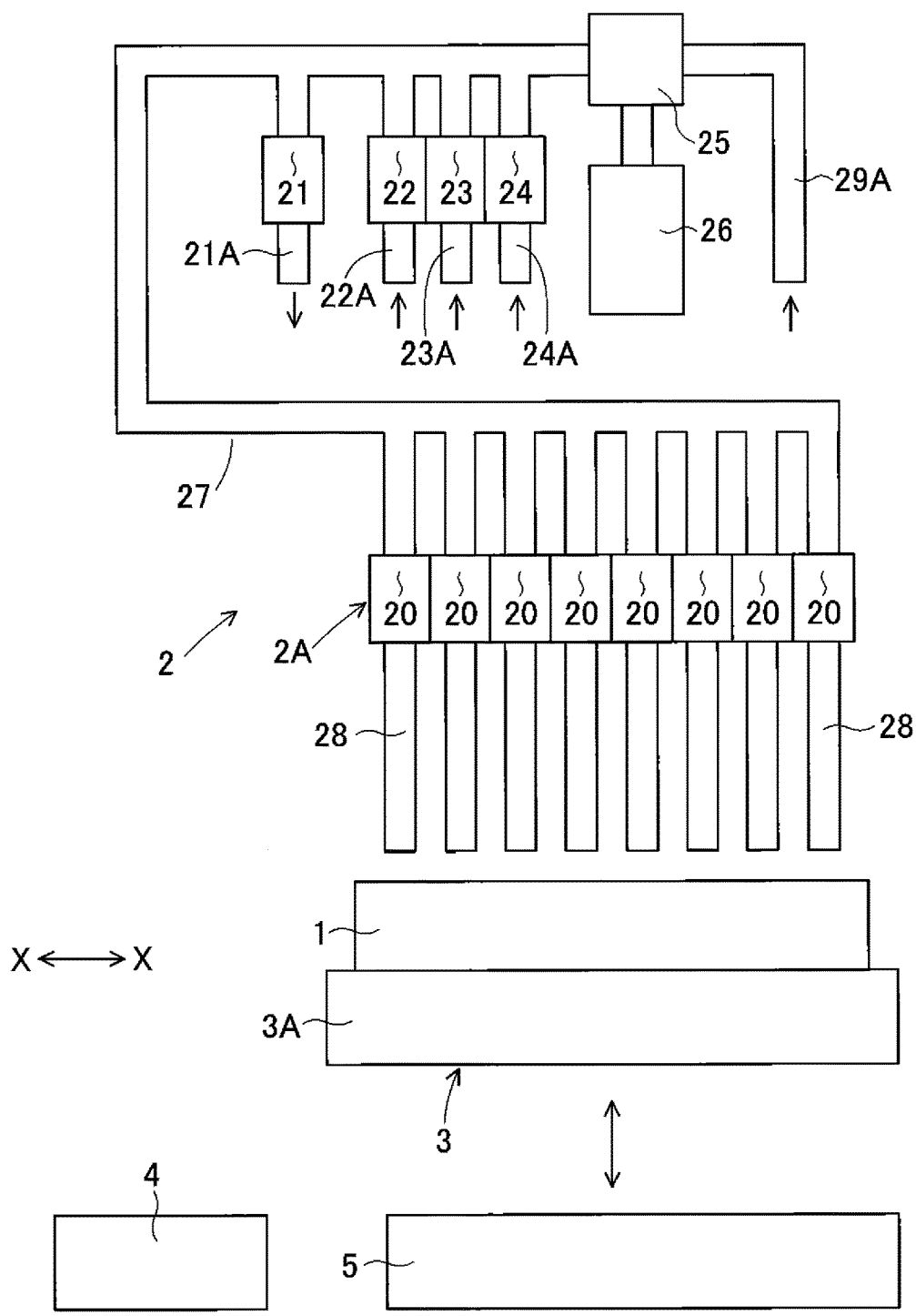
FIG. 1 is a schematic block diagram illustrating an imaging little fish management device of an embodiment.

A preferred embodiment of the present invention will be described with reference to the drawings. However, the present invention is not limited to the embodiment. A device illustrated in FIG. 1 includes an imaging plate 1, a water unit 2, a drive unit 3, a controller 4, and an imaging unit 5.

First, the imaging plate 1 will be generally described. The imaging plate 1 includes a plurality of wells and a plurality of sub-wells which are each opened upward. One zebrafish is accommodated in each well together with water. A lowermost portion of each well communicates with a lowermost portion of each sub-well adjacent thereto through discharge holes. However, the wells, the sub-wells, and the discharge holes are not illustrated in the schematic block diagram shown in FIG. 1. Shapes of the wells, the sub-wells, and the discharge holes will be described in detail later.

The water unit 2 includes a pipe 27 to which a nozzle valves 20, a discharge valve 21, suction valves 22 to 24, a three-way valve 25 and a syringe pump 26 are connected. The discharge valve 21, the suction valves 22 to 24, the three-way valve 25, and the syringe pump 26 correspond to an example of a water supply and discharge mechanism that transfers water to the imaging plate 1 through the nozzle valves 20, and it is clear that the same function can be configured with other known mechanisms. The valves 20 to 25 which are each configured with an electromagnetic valve are opened and closed based on an instruction given by the controller 4. The eight nozzle valves 20 individually control the communication between the upstream pipe 27 and eight nozzles 28. The eight nozzle valves 20 built in a nozzle head 2A are horizontally arranged in a column direction X so as to be adjacent to one another.

The eight nozzles 28 drooped from the nozzle head 2A are also arranged in the column direction X by the pitch of one well. The nozzle head 2A disposed just above the imaging plate 1 can be moved upward and downward by a nozzle drive unit (not illustrated). When the nozzle head 2A moves downward, each nozzle 28 is individually inserted into each sub-well of the imaging plate 1.

The discharge valve 21 which includes a water discharge pipe 21A drooped into a water discharge bottle (not illustrated) is opened when water inside the pipe 27 is discharged to the water discharge bottle. The suction valve 22 which includes a suction pipe 22A drooped into a breeding water bottle (not illustrated) is opened when breeding water having a predetermined component is suctioned from the breeding water bottle to the pipe 27. The suction valve 23 which includes a suction pipe 23A drooped into a feeding water bottle (not illustrated) is opened when water containing prey is suctioned from the feeding water bottle to the pipe 27.

The suction valve 24 which includes a suction pipe 24A drooped into an anesthesia water bottle (not illustrated) is opened when anesthesia water that is water containing an anesthetic is suctioned from the anesthesia water bottle to the pipe 27. The three-way valve 25 causes a syringe of the syringe pump 26 to communicate with any one of the pipe 27 and a pure water pipe 29A. The syringe pump 26 includes a piston which is driven linearly in an electromagnetic manner.

Hereinafter, a basic operation for the water unit 2 will be described. First, a pure water supply operation for supplying pure water inside the pure water pipe 29A to the pipe 27 will be described. The pure water supply operation is performed, for example, when an amount of the pure water existing in an upstream pipe portion or the like of the pipe 27 becomes less than an amount at a predetermined value. After the three-way valve 25 causes the syringe pump 26 and the pure water pipe 29A to communicate with each other, the syringe pump 26 suctions the pure water inside the pure water pipe 29A into the syringe. Next, after the three-way valve 25 causes the syringe pump 26 and the pipe 27 to communicate with each other, the syringe pump 26 pushes the pure water inside the syringe into the pipe 27. Accordingly, a predetermined amount of the pure water is always held in the upstream portion or the like of the pipe 27. When the pure water supply operation is not performed, the three-way valve 25 causes the syringe pump 26 and the pipe 27 to communicate with each other.

Next, an external water discharge operation for discharging water inside the wells (also referred to as well water) to the outside will be described. The nozzles 28 are inserted into the sub-wells of the imaging plate 1, respectively. After the nozzle valves 20 are opened, the syringe pump 26 suctions the well water inside the sub-wells to the pipe 27. Next, after the nozzle valves 20 are closed and the discharge valve 21 is opened, the syringe pump 26 pushes the water inside the pipe 27 out through the discharge valve 21. Accordingly, the well water inside the pipe is discharged to the outside.

Next, a breeding water supply operation for supplying the breeding water to the wells will be described. According to the embodiment, normal water filtered by a filter is used as the breeding water. First, after only the suction valve 22 is opened, the breeding water is suctioned into the pipe 27 by the syringe pump 26. Next, after the suction valve 22 is closed and the nozzle valves 20 are opened, the breeding water inside the pipe 27 is ejected from each nozzle 28 to each sub-well by the syringe pump 26. Note that, when the water levels of the sub-wells are high or a breeding water supply amount is large before the ejection, the external water discharge operation can be performed in advance so as to decrease the water levels of the sub-wells.

Next, a feeding water supply operation for supplying the water containing prey to the wells will be described. The water containing prey mentioned here means water mixed with powdered prey or microorganisms for prey. First, after only the suction valve 23 is opened, the water containing prey is suctioned into the pipe 27 by the syringe pump 26.

Next, after the suction valve 23 is closed and the nozzle valves 20 are opened, the water containing prey inside the pipe 27 is ejected from each nozzle 28 to each sub-well by the syringe pump 26. Note that, when the water levels of the sub-wells are high or a supply amount of the water containing prey is large before the ejection, the external water discharge operation can be performed in advance so as to decrease the water levels of the sub-wells.

Next, an anesthesia water supply operation for supplying the anesthesia water to the wells will be described. The anesthesia water mentioned here means water containing an anesthetic. First, after only the suction valve 24 is opened, the anesthesia water is suctioned into the pipe 27 by the syringe pump 26. Next, after the suction valve 24 is closed and the nozzle valves 20 are opened, the anesthesia water inside the pipe 27 is ejected from each nozzle 28 to each sub-well by the syringe pump 26. Note that, when the water levels of the sub-wells are high or an anesthesia water supply amount is large before the ejection, the external water discharge operation can be performed in advance so as to decrease the water levels of the sub-wells. The external water discharge operation, the breeding water supply operation, the feeding water supply operation, and the anesthesia water supply operation are controlled by the controller 4.

According to the embodiment, the imaging plate 1 is placed on a base 3A of the drive unit 3. The drive unit 3 includes a built-in drive device (not illustrated) that horizontally moves the base 3A by the pitch of one well in a row direction Y perpendicular to the column direction X. The horizontal movement of the imaging plate 1 is executed while the nozzle head 2A is retracted upward. The drive unit 3 can also be omitted by moving the nozzle head 2A in the row direction Y instead of the imaging plate 1. According to the aspect of moving the nozzle head 2A, it is preferable to also move the imaging unit 5 in the row direction Y.

The imaging unit 5 includes a UV lamp, an imaging device, and an optical system. The optical system irradiates each well through a transparent bottom portion of each well with a UV ray emitted from the UV lamp. Further, the optical system guides fluorescence emitted from the zebrafishes to the imaging device. According to the embodiment, the imaging unit 5 simultaneously images the eight wells arranged in the column direction X. In addition, the eight wells arranged in the column direction X can also be sequentially imaged, and the wells of a plurality of rows adjacent to one another can also be simultaneously imaged. All the wells can also be simultaneously imaged by using an improved optical system.

Further, the imaging unit 5 includes a built-in image processor that processes imaged images. According to the embodiment, the image processor has a function of determining whether positions or posture of the zebrafishes extracted from the imaged images are good or not.

Figure 2:
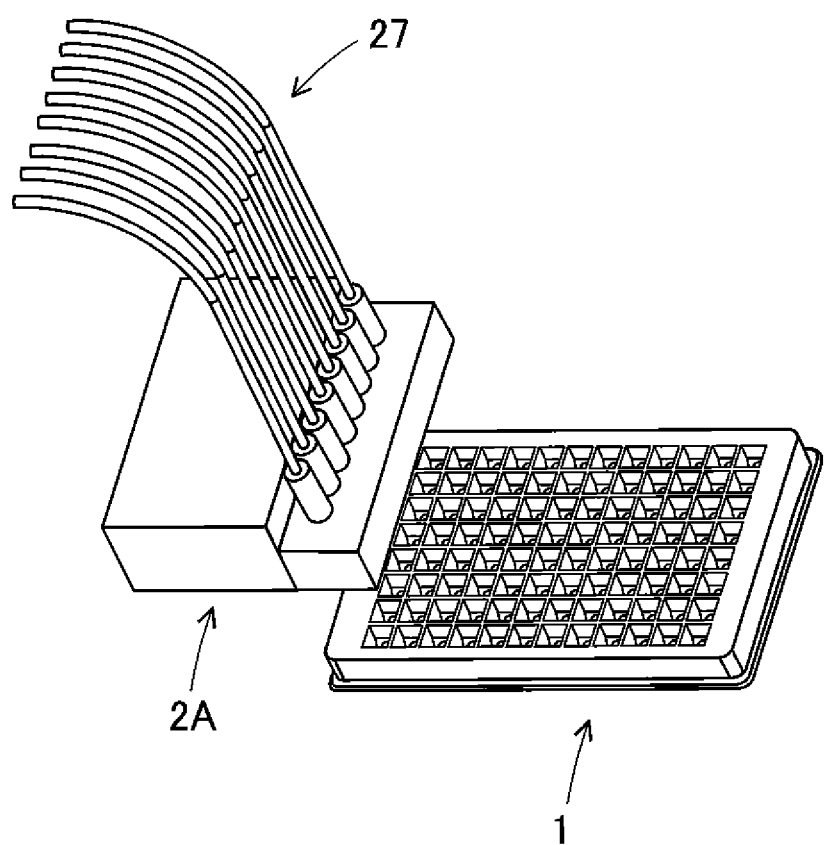
FIG. 2 is a perspective view illustrating an example of a nozzle head and an imaging plate.

The controller 4 controls the operations of the water unit 2, the drive unit 3, and the imaging unit 5 based on a program stored in advance. FIG. 2 is a perspective view illustrating an example of the nozzle head 2A and the imaging plate 1. According to FIG. 2, the valves 21 to 24, the three-way valve 25, and the syringe pump 26 illustrated in FIG. 1 are separately provided for each nozzle valve 20. Accordingly, a zebrafish breeding environment can be easily changed every column.

Figure 3:
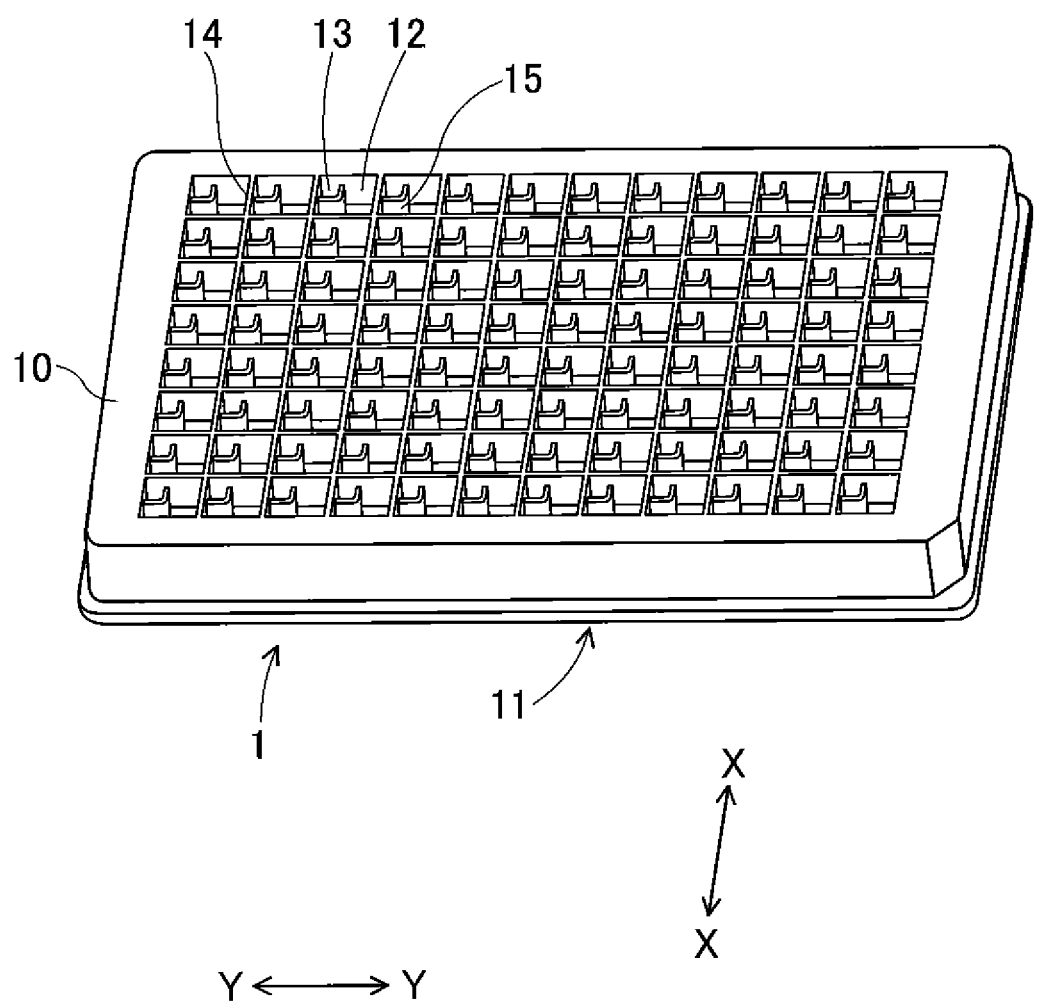
FIG. 3 is an enlarged perspective view illustrating the imaging plate.

A detailed structure of the imaging plate 1 adopted in the embodiment will be described with reference to FIGS. 3 to 6. FIG. 3 is an enlarged perspective view illustrating the imaging plate 1. The resinous imaging plate 1 includes a thick well array plate 10 and a transparent bottom plate 11 which is bonded to a lower surface of the well array plate 10. The well array plate 10 includes ninety six wells 12 arranged in a matrix shape. The well array plate 10 includes a partition wall portion 14 which has a lattice shape and defines each well 12 and an overflow bottom wall portion 15 which defines each sub-well 13 together with the partition wall portion 14.

The overflow bottom wall portion 15 which is an L-shaped wall and is provided at one corner of each well 12 defines each sub-well 13 inside each well 12. The wells 12 and the sub-wells 13 which are opened upward reach the transparent bottom plate 11. The overflow bottom wall portion 15 is formed so as to be lower than the partition wall portion 14.

Figure 4:
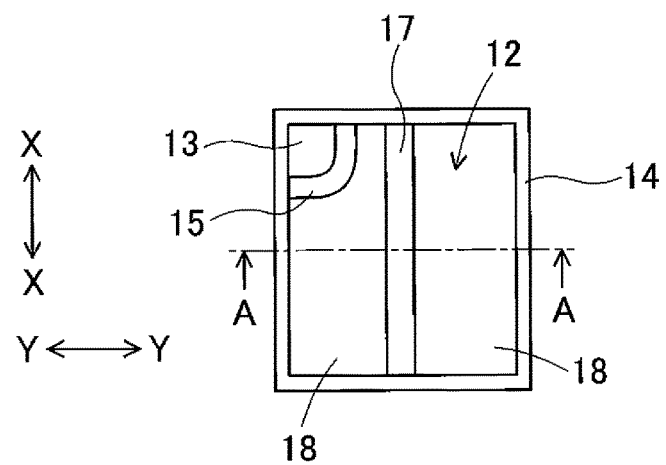
FIG. 4 is schematic plan view illustrating one well 12 and one sub-well 13.
Figure 5:
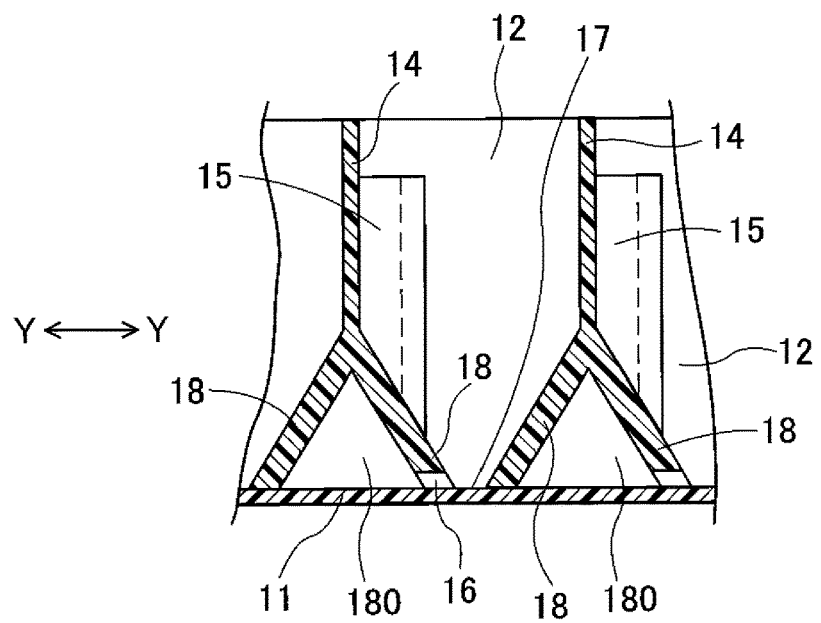
FIG. 5 is a schematic cross-sectional view taken along line A-A of the well 12 illustrated in FIG. 4.

Detailed shapes of each well 12 and each sub-well 13 will be described with reference to FIGS. 4 and 5. FIG. 4 is a schematic plan view illustrating the one well 12 and the one sub-well 13. FIG. 5 is a schematic cross-sectional view taken along line A-A of the well 12 illustrated in FIG. 4. A lower portion of the partition wall portion 14 formed in a lattice shape is branched into two so as to configure a pair of inclined surface portions 18. Accordingly, the width of the well 12 in the row direction is gradually decreased toward the transparent bottom plate 11 by the pair of inclined surface portions 18 interposing the well 12 therebetween. In other words, an upper portion of the well 12 has a square cylindrical shape, and a lower portion of the well 12 has a substantially inverse roof shape.

A bottom portion 17 of the well 12 faces the transparent bottom plate 11, and is interposed between the pair of inclined surface portions 18 to have a rectangular shape. A long side edge of the bottom portion 17 is formed so as to be longer than the maximum length of the zebrafish, and a short side edge thereof is formed so as to be shorter than the maximum length of the zebrafish. Further, a water storage portion 180 having a triangular prism shape is defined by the transparent bottom plate 11 and the pair of inclined surface portions 18 which are branched from the one partition wall portion 14.

One of the inclined surface portions 18 is adjacent to the overflow bottom wall portion 15 as the L-shaped wall, and is integrally formed with the overflow bottom wall portion 15. Since a lower opening of the sub-well 13 communicates with the water storage portion 180, the water storage portion 180 is considered as a portion of the sub-well 13.

Among the two inclined surface portions 18 interposing the one well 12 therebetween, a lower end of the one inclined surface portion 18 integrally formed with the overflow bottom wall portion 15 faces the transparent bottom plate 11 through a plurality of discharge holes 16. In other words, the plurality of discharge holes 16 is provided between the transparent bottom plate 11 and the one inclined surface portion 18 integrally formed with the overflow bottom wall portion 15. The plurality of discharge holes 16 is formed below the one inclined surface portion 18 integrally formed with the overflow bottom wall portion 15, and is arranged at a predetermined pitch in the column direction X. The discharge holes 16 each have a cross-sectional shape that does not enable the zebrafish to pass therethrough and that enables feces or prey of the zebrafish to pass therethrough. Consequently, the discharge holes 16 cause a lower end of the well 12 to communicate with a lower end of the water storage portion 180.

Figure 6:
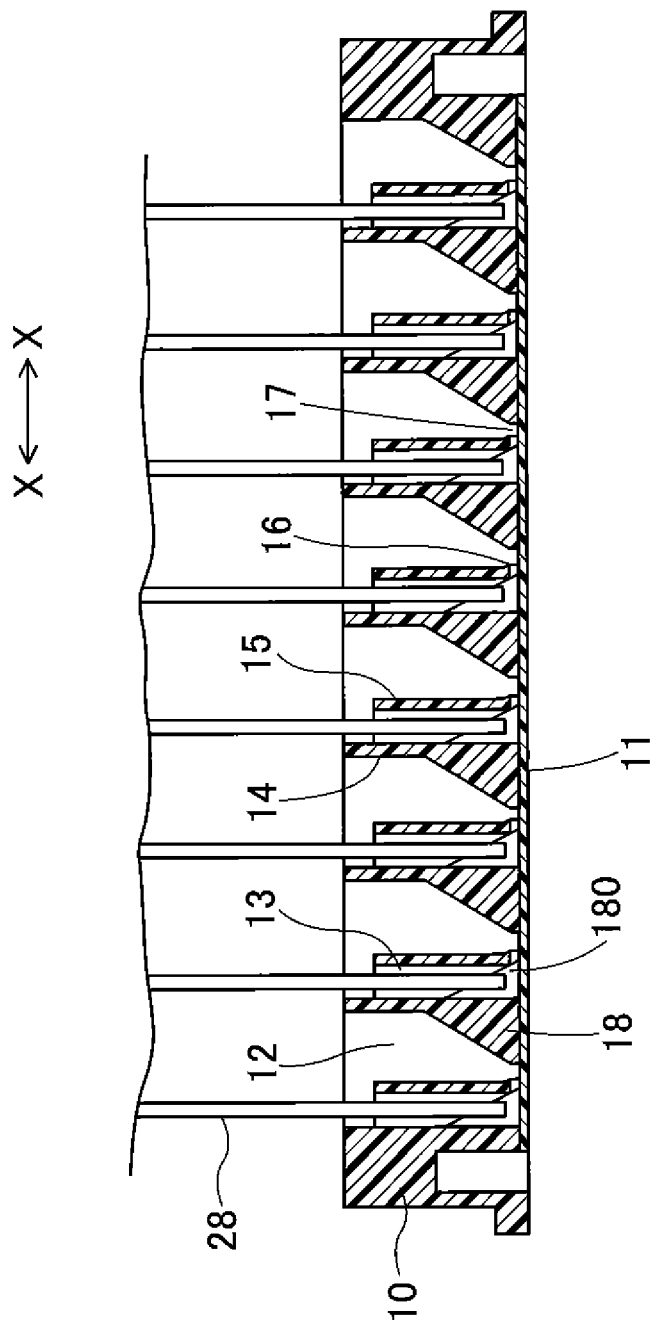
FIG. 6 is a schematic cross-sectional view illustrating the imaging plate into which a nozzle is inserted.

FIG. 6 is a schematic cross-sectional view illustrating a state where the eight nozzles 28 which are drooped from the nozzle head 2A are individually inserted into the eight sub-wells 13 of the imaging plate 1. However, since each inclined surface portion 18 illustrated in FIG. 6 is formed so as to be thicker downward, the water storage portion 180 illustrated in FIG. 6 has a smaller volume than that of the water storage portion 180 illustrated in FIG. 5.

An imaging capturing control routine which is performed by the controller 4 will be described with reference to a flowchart illustrated in FIG. 7. First, an anesthesia operation for simultaneously putting the zebrafishes accommodated in the wells 12 to sleep is performed (step S100). According to the anesthesia operation, after the nozzles 28 are respectively inserted into the sub-wells 13 of the first row, the anesthesia water is injected into the sub-wells 13 of the first row by an anesthesia water supply operation. Note that, when the water levels of the sub-wells 13 are high, an external water discharge operation is executed before the anesthesia water supply operation.

Accordingly, the zebrafishes inside the wells 12 of the first row becomes in a sleep state. Subsequently, all the zebrafishes are anaesthetized by performing the anesthesia water supply operation while the imaging plate 1 is relatively moved by the pitch of one well with respect to the nozzles 28.

Next, a row imaging sub-routine of imagining the eight zebrafishes accommodated in the wells 12 of one row will be described below. The row imaging sub-routine includes a preliminary water discharge operation (step S102), a water supply operation (step S104), a secondary water discharge operation (step S106), and an imaging operation (step S108).

First, the preliminary water discharge operation will be described. The nozzles 28 are individually inserted into the sub-wells 13, and thereafter the external water discharge operation is executed, whereby the water of the wells 12 of this row is discharged through the sub-wells 13. Accordingly, downward water streams are formed inside the wells 12, and the water levels of the wells 12 decrease. Due to the preliminary water discharge operation, the zebrafishes move downward to a nearly settling position. The inclined surface portions 18 guide the zebrafishes to the bottom portions 17 of the wells 12.

Next, the water supply operation will be described. The breeding water is supplied to the sub-wells 13 of this row by executing the breeding water supply operation. Since the breeding water is jetted out of the sub-wells 13 through the discharge holes 16 to the lower portions of the wells 12 in the lateral direction, whirling water streams are formed in the longitudinal sections of the wells 12. Since the zebrafishes which exist in the vicinities of the bottom portions 17 of the wells 12 are biased in a direction where fluid resistance to the water streams decreases, the zebrafishes lie on the bottom portions 17.

However, since the discharge holes 16 are narrow, the water levels of the sub-wells 13 abruptly increase when the nozzles 28 eject the breeding water into the sub-wells 13. As a result, the water of the sub-wells 13 overflows the overflow bottom wall portions 15 and enters the wells 12 communicating with the sub-wells through the discharge holes 16. However, since the overflow bottom wall portions are formed so as to be lower than the partition wall portions 14 between the wells 12, the water of the sub-wells 13 does not overflow into the other wells 12.

Next, the secondary water discharge operation will be described. The external water discharge operation is executed again, and the water level of each well 12 decreases. Accordingly, the zebrafishes of this row are completely settled on the bottom portions 17.

Next, the imaging operation in which the imaging unit 5 images the zebrafishes of this row is performed, and the imaged images are processed (step S108). Next, it is determined whether a lying posture and a lying position of each zebrafish obtained by the image processing are good or not (step S110). When it is determined that the lying posture and the lying positions of the zebrafishes are poor, step S102 to step S108 are performed again only on the zebrafishes determined to be in a poor posture and position. That is, the nozzle valves 20 corresponding to the wells in which the zebrafishes are determined to be in a good posture and position are always kept closed. Accordingly, the poor lying posture and lying positions of the zebrafishes are noticeably improved. If a lying success ratio of the zebrafishes of one row is 80% when the row imaging sub-routine is executed once, a lying success ratio of the zebrafishes of one row becomes 96% when the row imaging sub-routine is executed again on the zebrafishes determined to be in the poor posture and position.

When the image determination result reaches a predetermined level or more, the process proceeds to step S112. In step S112, it is determined whether the wells 12 of all rows are imaged. When the determination result is No, the imaging plate 1 is shifted by the pitch of one well (step S114), and the row imaging sub-routine is performed on the zebrafishes of the next row. When it is determined that the wells 12 of the last row are imaged, an awakening operation is executed (step S116). According to the awakening operation, each of the external water discharge operation and the breeding water supply operation is performed once or more, and the water of all the wells 12 and all the sub-wells 13 is replaced with the breeding water. Accordingly, all the zebrafishes are awakened again.

Figure 7:
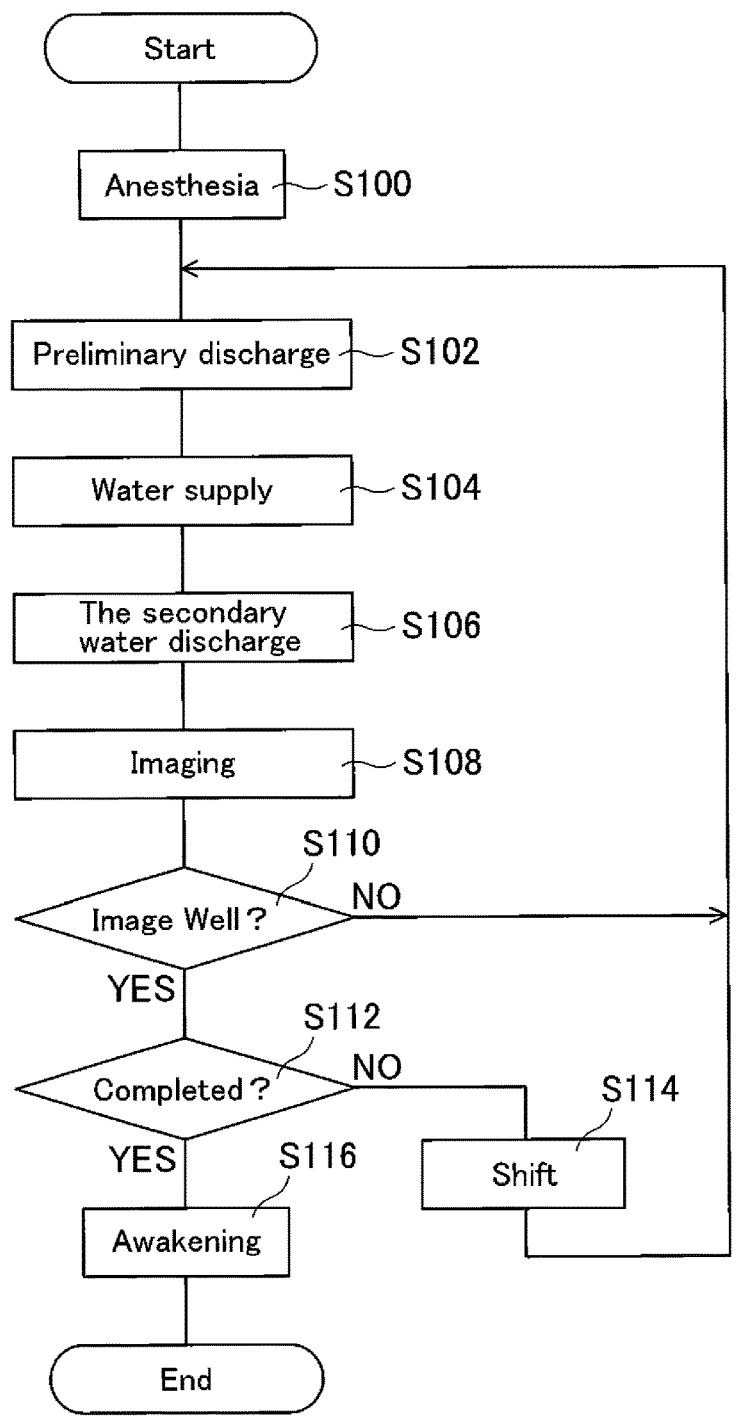
FIG. 7 is a flowchart illustrating an imaging capturing control routine.

Note that, according to the flowchart illustrated in FIG. 7, the zebrafishes are imaged every row, but of course, the imaging capturing control routine is not limited thereto. For example, the preliminary water discharge operation may be performed on all the sub-wells 13, and thereafter the water supply operation may be performed on all the sub-wells 13. Subsequently, the secondary water discharge operation may be performed on all the sub-wells 13.

Figure 8:
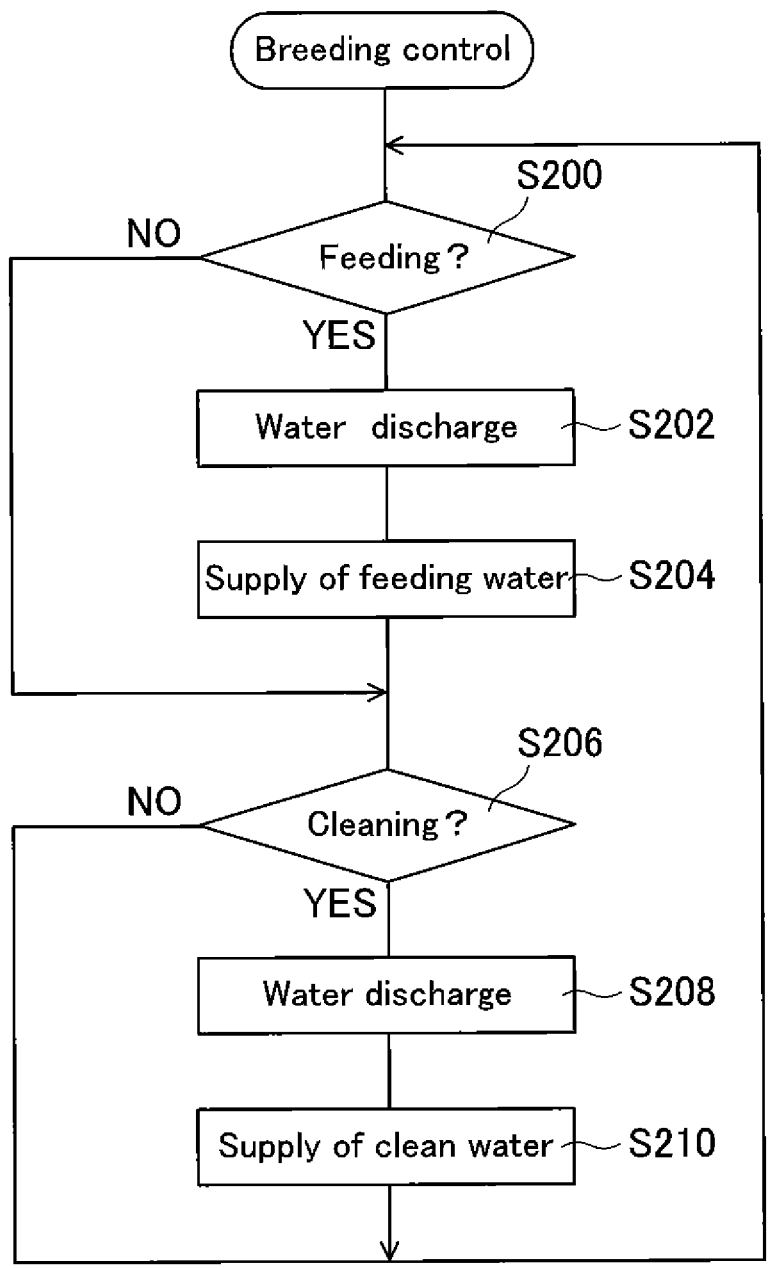
FIG. 8 is a flowchart illustrating a breeding control routine.

A breeding control routine which is performed by the controller 4 will be described with reference to a flowchart illustrated in FIG. 8. The breeding control routine is periodically performed. However, FIG. 8 illustrates only feeding the zebrafishes accommodated in the wells 12 of one row and replacing the water thereof. It is clear that the breeding control routine can be performed on the zebrafishes of each row by moving the imaging plate 1 by the pitch of one well while moving the nozzle head 2A upward and downward.

First, it is determined whether the zebrafishes are to be fed (step S200). When it is determined that the zebrafishes are to be fed, the external water discharge operation is performed (step S202), and subsequently the feeding water supply operation is executed (step S204). When it is determined that the zebrafishes are not to be fed, the process proceeds to step S206. Accordingly, the zebrafishes are fed. Note that, when the water levels of the wells 12 are low, the external water discharge operation can be omitted.

Next, it is determined whether the water inside the wells 12 is to be replaced (step S206). When it is determined that the water is to be replaced, the external water discharge operation is performed (step S208), and subsequently the breeding water supply operation is executed (step S210). When it is determined that the water is not to be replaced, the process returns to step S200. Accordingly, the water inside the wells 12 and the sub-wells 13 is replaced as necessary. Consequently, since the water supply and discharge at the time of imaging illustrated in FIG. 7 and the feeding and water replacement illustrated in FIG. 8 are performed by using the common water unit 2, it is understood that the configuration of the device becomes largely simplified.

Figure 9:
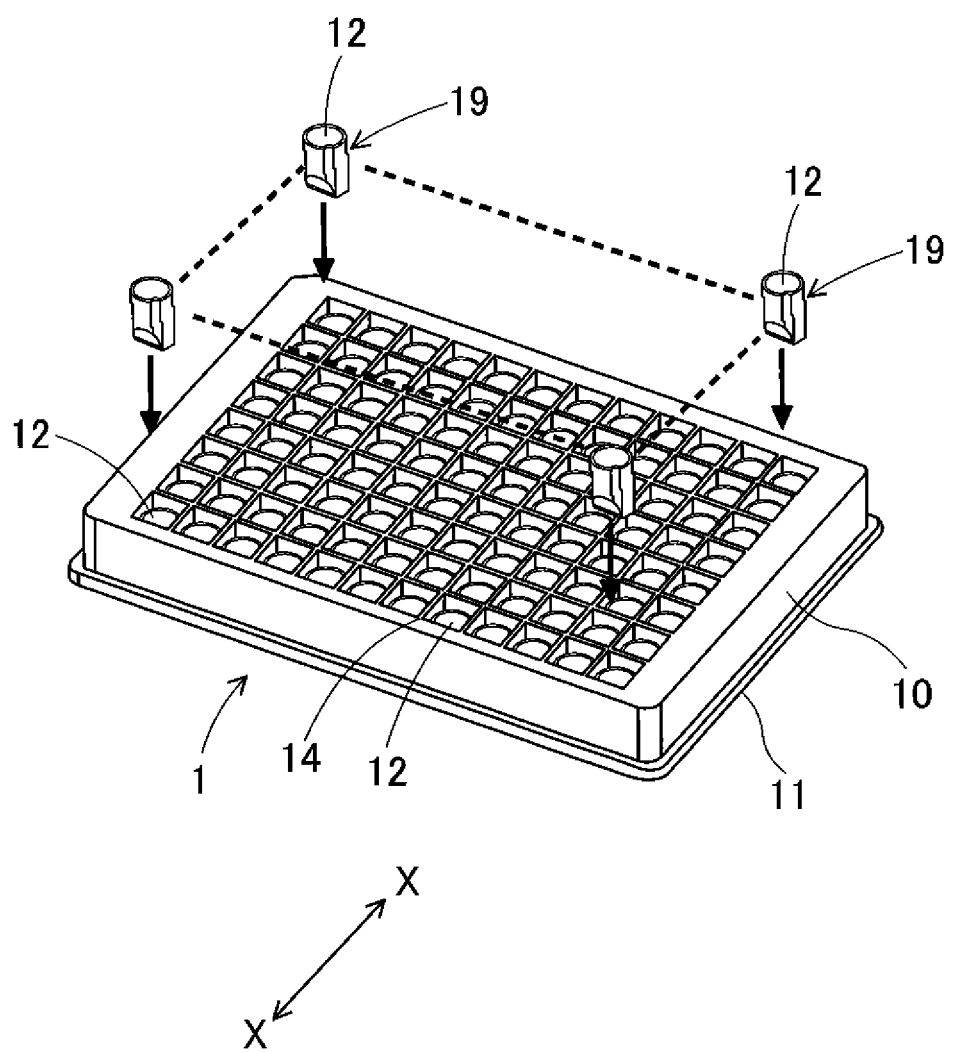
FIG. 9 is a perspective view illustrating a modification of an imaging plate.

A modification of an imaging plate 1 will be described with reference to FIGS. 9 to 11. FIG. 9 is a perspective view illustrating the imaging plate 1. A well array plate 10 of the imaging plate 1 includes a partition wall portion 14 formed in a lattice shape, and the partition wall portion 14 forms a plurality of rectangular penetration holes arranged in a matrix shape. A lower end side opening of each rectangular penetration hole is shielded by a transparent bottom plate 11. An auxiliary tube member 19 which includes a well 12 inside thereof and has a substantially cylindrical shape is inserted into each penetration hole. As a result, a sub-well 13 is formed between the auxiliary tube member 19 and a partition wall portion 14. However, the sub-well 13 is not illustrated in FIG. 9.

Figure 10:
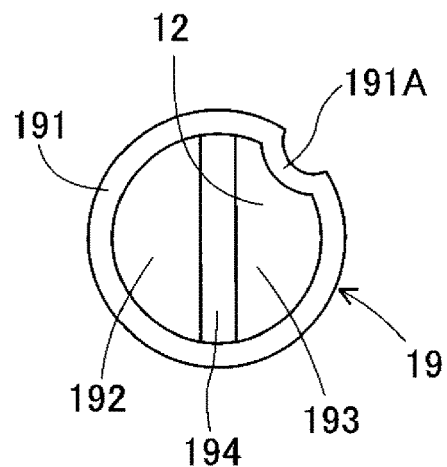
FIG. 10 is a plan view illustrating an auxiliary tube member.
Figure 11:
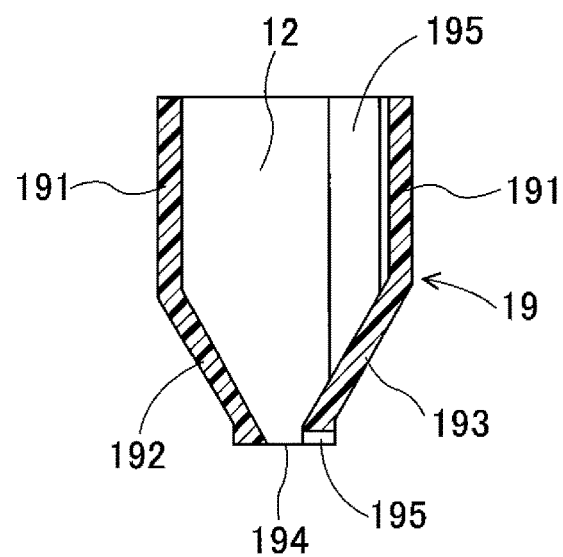
FIG. 11 is a longitudinal sectional view illustrating the auxiliary tube member.

FIG. 10 is a plan view illustrating the auxiliary tube member 19, and FIG. 11 is a longitudinal sectional view of the auxiliary tube member 19. The auxiliary tube member 19 includes the well 12 which is surrounded by a peripheral wall portion 191 having a substantially cylindrical shape. A lower portion of the peripheral wall portion 191 includes a pair of inclined surface portions 192 and 193 which are inclined so as to narrow the horizontal width of the well 12.

The well 12 includes a rectangular opening 194 interposed between the inclined surface portion 192 and the inclined surface portion 193. Therefore, the transparent bottom plate 11 which faces the opening 194 configures a bottom portion of the well 12. A lower end of the inclined surface portion 193 is formed so as to be slightly higher than a lower end of the inclined surface portion 192. Accordingly, a discharge hole 195 is formed between the lower end of the inclined surface portion 193 and the transparent bottom plate 11.

The peripheral wall portion 191 of the auxiliary tube member 19 is formed so as to be lower than the partition wall portion 14. Accordingly, the peripheral wall portion 191 configures an overflow bottom wall portion of the present invention. Further, a portion 191A of the peripheral wall portion 191 is depressed as illustrated in FIG. 10. Accordingly, it becomes easy to insert a nozzle 28 into the sub-well 13 between the partition wall portion 14 and the portion 191A of the peripheral wall portion 191.

Figure 12:
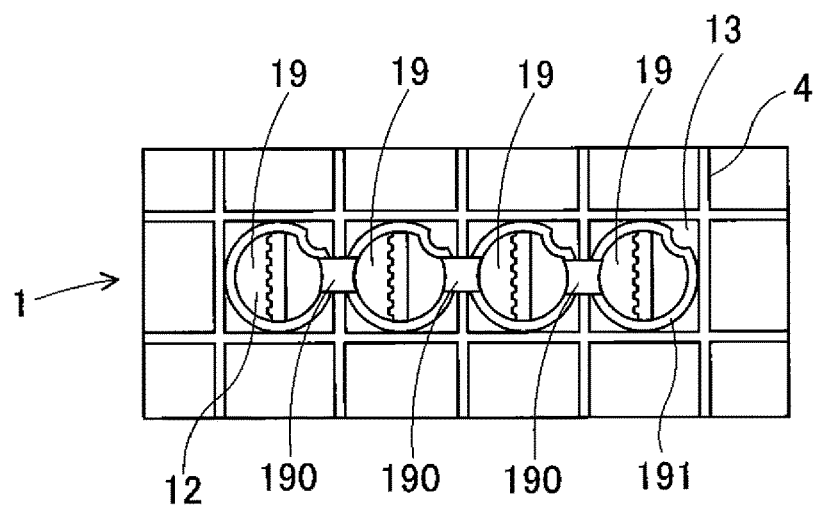
FIG. 12 is a partial plan view illustrating another modification of an imaging plate.
Figure 13:
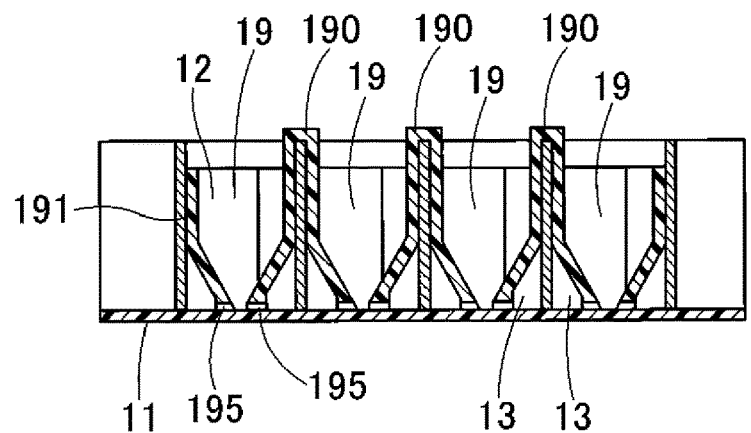
FIG. 13 is a partially longitudinal sectional view illustrating the imaging plate illustrated in FIG. 12.

Another modification of an imaging plate 1 will be described with reference to FIGS. 12 and 13. FIG. 12 is a partial plan view illustrating a portion of the imaging plate 1. FIG. 13 is a partially longitudinal sectional view of the imaging plate 1. In the imaging plate 1, four auxiliary tube members 19 arranged in series are connected by connection portions 190. The connection portion 190 extending from an upper end of a peripheral wall portion 191 of the one auxiliary tube member 19 climes over a partition wall portion 14, and reaches the upper end of the peripheral wall portion 191 of the next auxiliary tube member 19. Accordingly, it becomes easy to assemble the imaging plate 1.

The peripheral wall portion 191 of the auxiliary tube member 19 illustrated in FIGS. 9 to 13 is substantially cylindrical, but is not limited to this shape. The peripheral wall portion may have a square shape having a size substantially equal to the space surrounded by the partition wall portion 14 of the imaging plate 1 illustrated in FIG. 9. A shape of the auxiliary tube member in that case is similar to those of the well 12 and the sub-well 13 illustrated in FIGS. 5 and 6.

The modified example will be described below. First, it is desirable to introduce the zebrafish into the well 12 along with the anesthetic solution. At this time, the anesthetic solution inside the well 12 tends to flow to the sub-well 13 through the discharge holes 16 communicating the bottom portion of the well 12 with the bottom portion of the sub-well 13. However, since the diameter of the discharge hole 16 is very small and the surface tension of the anesthetic solution disturbs the flow, there is a case where the anesthetic solution inside the well 12 does not smoothly flow to the sub-well 13.

One answer for this problem is to use a centrifugal force. The imaging plate 1 is fixed to a horizontal rotation base having a rotation shaft extending in the vertical direction. The sub-well 13 which communicates with the well 12 by the discharge holes 16 are disposed at the outside of the well 12 in the radial direction. In other words, the sub-well 13 is disposed at a position far from the rotation shaft in relation to the well 12.

Accordingly, the anesthetic solution may flow to the sub-well 13 through the discharge holes 16 by the centrifugal force applied to the anesthetic solution of the well 12. As a result, the anesthetic solution is charged in the discharge holes 16 and flows to the sub-well 13. Further, when the rotation time is extended, most of water inside the well 12 moves to the sub-well 13. For this reason, the zebrafish inside the well 12 is satisfactorily laid on the bottom surface of the well 12.

Another answer for the problem is to use a pressure difference. The anesthetic solution and the zebrafish are introduced into the well 12, and the anesthetic solution is introduced into the sub-well 13. Next, a thin tube is inserted into the sub-well 13. It is desirable that the tip of the thin tube reach the vicinity of the bottom portion of the sub-well 13. When the anesthetic solution is rapidly suctioned from the thin tube, the pressure at the outlet of the discharge hole 16 decreases, and hence the discharge hole 16 may be opened. When the suctioning operation is continued, the anesthetic solution inside the well 12 is suctioned into the thin tube through the discharge hole 16. As a result, the water level inside the well 12 decreases, and hence the zebrafish may be laid on the bottom surface of the well 12.

What is claimed is:

1. A device comprising:
an imaging plate for performing a vertical view imaging of fishes, comprising:
a plurality of wells for holding a fish in each of the wells and for holding water when desired,
wherein each well has a rectangular shaped transparent bottom portion for imaging of a fish held in the well,
wherein the rectangular shape of the transparent bottom portion has two opposing long side edges and two opposing short side edges,
wherein the long side edges are longer than the fish and the short side edges are shorter than the fish, so as to individually accommodate optical examination of the fish through the transparent bottom portion when the well is holding the fish;
a transparent bottom plate forming the transparent bottom portions of the plurality of wells;
a partition wall portion defining each of the wells such that the wells are arranged in a matrix,
wherein in each of the wells, the partition wall portion has two opposing sides that form a pair of inclined surface portions that define the rectangular shape of the transparent bottom portion and also gradually reduces the width of the well toward the transparent bottom portion of the well for guiding the fish toward the transparent bottom portion and settling and orienting the fish within the rectangular shape when there is no water in the well;

a water storage portion provided for each of the wells, defined by the transparent bottom plate and two adjacent inclined surface portions of the partition wall and positioned adjacent to its corresponding well;

an overflow bottom wall extending upward from the water storage portion within each of the wells and defining a water storage sub-well above the water storage potion in each of the wells between a portion of the partition wall portion and the overflow bottom wall, wherein the water storage sub-well is in fluid communication with the water storage portion for supplying water to the well;

a discharge hole connecting each of the wells and its corresponding water storage portion, wherein the discharge hole is provided in the inclined surface portion in each of the wells adjacent to the transparent bottom portion and extending in a horizontal direction between the water storage portion and the well and allowing the well to be in fluid communication with the water storage portion for supplying water to and removing water from the well, each of the discharge holes having a cross-sectional shape that does not allow the fish to pass therethrough, wherein the fluid communication among the water storage sub-well, the water storage portion, and the well enables introduction of water to the well by introducing water into the water storage sub-well and enables removal of water from the well by extracting water through the water storage sub-well; and a nozzle provided for each of the plurality of wells for performing water supply operations supplying water to the well via the water storage sub-well, as well as performing water discharge operations removing water from the well via the water storage sub-well.

2. The device according to claim 1, wherein in each well the discharge hole is formed adjacent to the long side edge of the bottom portion.

3. The device according to claim 1, wherein the overflow bottom wall is shorter than the partition wall portion, whereby when the water storage sub-well is overfilled with water, the water in the sub-well overflows into the well.

4. The device according to claim 1, wherein the discharge hole has a cross-sectional shape that enables prey for each of the fishes and feces of each of the fishes to pass through the discharge hole, and the water control unit performs a water replacement operation for replacing the water inside the wells in order to allow the fishes inside the wells to survive for a predetermined period.

5. The device for imaging fish according to claim 1, wherein in the matrix shaped arrangement of the wells, the wells are aligned with the rectangular shape of the transparent bottom portion of the wells in a direction that matches one another and thereby all of the fishes settled in the rectangular shaped transparent bottom portion of the wells are in parallel direction to one another.

6. The device for imaging fish according to claim 1, wherein the rectangular shaped transparent bottom portion of each well having a concave shape that guides a fish in the well to a center portion of the bottom portion.

7. A plate for imaging fish and for performing a vertical view imaging of fishes, comprising:

a plurality of wells for holding a fish in each of the wells and for holding water when desired, wherein each well has a rectangular shaped transparent bottom portion for imaging of a fish held in the well, wherein the rectangular shape of the transparent bottom portion has two opposing long side edges and two opposing short side edges, wherein the long side edges are longer than the fish and the short side edges are shorter than the fish, so as to individually accommodate optical examination of the fish through the transparent bottom portion when the well is holding the fish;

a transparent bottom plate forming the transparent bottom portions of the plurality of wells;

a partition wall portion defining each of the wells such that the wells are arranged in a matrix, wherein in each of the wells, the partition wall portion has two opposing sides that form a pair of inclined surface portions that define the rectangular shape of the transparent bottom portion and also gradually reduces the width of the well toward the transparent bottom portion of the well for guiding the fish toward the transparent bottom portion and settling and orienting the fish within the rectangular shape when there is no water in the well;

a water storage portion provided for each of the wells, defined by the transparent bottom plate and two adjacent inclined surface portions of the partition wall and positioned adjacent to its corresponding well;

an overflow bottom wall extending upward from the water storage portion within each of the wells and defining a water storage sub-well above the water storage potion in each of the wells between a portion of the partition wall portion and the overflow bottom wall, wherein the water storage sub-well is in fluid communication with the water storage portion for supplying water to the well, wherein the overflow bottom wall is shorter than the partition wall portion; and a discharge hole connecting each of the wells and its corresponding water storage portion, wherein the discharge hole is provided in the inclined surface portion in each of the wells adjacent to the transparent bottom portion and extending in a horizontal direction between the water storage portion and the well and allowing the well to be in fluid communication with the water storage portion for supplying water to and removing water from the well, each of the discharge holes having a cross-sectional shape that does not allow the fish to pass therethrough, wherein the fluid communication among the water storage sub-well, the water storage portion, and the well enables supplying water to the well by introducing water into the water storage sub-well and enables removal of water from the well through the water storage sub-well.

8. The plate for imaging fish according to claim 7, wherein the discharge hole is oriented substantially parallel to the bottom plate while being adjacent to the long side edges of the bottom portion.

9. The plate for imaging fish according to claim 7, wherein the overflow bottom wall is lower than the partition wall portion causing water overflowing from the water storage sub-well to overflow into the well.

10. The plate for imaging fish according to claim 7, wherein in the matrix shaped arrangement of the wells, the wells are aligned with the rectangular shape of the transparent bottom portion of the wells in a direction that matches one another and thereby all of the fishes settled in the rectangular shaped transparent bottom portion of the wells are in parallel direction to one another.

11. The plate for imaging fish according to claim 7, wherein the rectangular shaped transparent bottom portion of each well having a concave shape that guides a fish in the well to a center portion of the bottom portion.

\* \* \* \* \*